United States Patent [19]

Kawarabayashi et al.

[11] Patent Number: 4,951,415

[45] Date of Patent: Aug. 28, 1990

[54] CULTURING APPARATUS

[75] Inventors: Waichiro Kawarabayashi; Koichi Matsubara; Toshihiro Yoshioka; Hikaru Yamagata; Shigeru Takahashi; Yukimasa Hirata; Yoshiko Shirane, all of Kuga, Japan

[73] Assignee: Mitsui Petrochemical Industries, Ltd., Tokyo, Japan

[21] Appl. No.: 216,863

[22] Filed: Jul. 7, 1988

[30] Foreign Application Priority Data

Jul. 7, 1987 [JP] Japan .................................. 62-170629
Apr. 30, 1988 [JP] Japan .................................. 63-108030

[51] Int. Cl.⁵ .............................................. A01G 31/00
[52] U.S. Cl. .......................................... 47/60; 47/59; 47/1.7
[58] Field of Search ............... 47/59, 60, DIG. 3, 5.5, 47/1.1, 58 (U.S. only), 73, 65, 1.4, 1.7; 83/123, 178, 181, 353; 241/28, 29, 46.02; 99/510, 635

[56] References Cited

U.S. PATENT DOCUMENTS 3,683,550 8/1972 Corlett, Jr. et al. ................... 47/58
4,350,768 9/1982 Tihon et al. ......................... 435/241

FOREIGN PATENT DOCUMENTS 0132414  1/1985  European Pat. Off. .
2310844  12/1976 France .
2340040  9/1977  France .................................. 47/65
2520190  7/1983  France .................................. 47/59
8503843  9/1985  PCT Int'l Appl. .................... 47/65
1144665  3/1985  U.S.S.R. ................................ 47/65
2118089A 10/1983 United Kingdom .

Primary Examiner—Robert A. Hafer
Assistant Examiner—Kerry Owens
Attorney, Agent, or Firm—Nixon & Vanderhye

[57] ABSTRACT

A culturing apparatus including a culturing tank for culturing cells, organs or tissue strips of a plant, internally therein, and a cutting device for cutting cultured plant bodies arranged within the culturing tank, wherein a push-out means for urging the plant bodies against the cutting device is further provided or the cutting means is made movable so as to be urged against the plant bodies.

9 Claims, 4 Drawing Sheets

CULTURING APPARATUS

BACKGROUND OF THE INVENTION

1. Field of the Invention

The present invention relates to a culturing apparatus equipped with a cutting device. More specifically, it relates to a culturing apparatus capable of obtaining new cultured strips to be provided for culturing, by cutting callus or plant bodies grown in a liquid culture medium or solid culture medium (hereinafter referred to as plant bodies) without removing the same from the culturing tank.

2. Description of the Related Art

The methods of culturing a tissue culture of plants include a method in which culturing is performed by using a solid culture medium such as agar, and a method using a liquid culture medium. The former method has an advantage in that a differentiating proliferation can be easily effected, and the latter method is advantageous in that the cultural materials need not be planted in the bed, but can be thrown into the medium, whereby troublesome labor is not required and the method is thus suitable for bulk cultivation. Nevertheless, in either method, when a material to be provided for cultivation must be obtained aseptically, for example, when scales of lily bulbs are to be cultured, the scales must be peeled from the bulbs, while sterilized under aseptic conditions such as on a clean bench, sheet by sheet by a scalpel and tweezers, and further, to improve the proliferation percentage, the scale must be finely cut with a scalpel, and thus considerable labor and time are required when obtaining cultured materials.

The situation is the same when the plant bodies obtained by cultivation are utilized as cultured materials and further culturing is desired by using these materials, and after the plant bodies differentiated and proliferated in liquid culture medium or a solid culture medium are aseptically taken out of the culturing device, strips of the cultured materials must be obtained by dissecting the plant bodies as described above.

When utilizing plant bodies obtained by cultivation and repeating culturing, according to the prior art method, the plant bodies must be taken out every time culturing is to be repeated and strips of the cultured material must be obtained manually.

To enable production on an industrial scale, desirably strips of the plant bodies which are to be used as the cultured materials are obtained.

SUMMARY OF THE INVENTION

Accordingly, the objects of the present invention are to eliminate the above-mentioned disadvantages of the prior art and to provide a culturing apparatus capable of obtaining cultured strips by cutting them aseptically without taking the grown plant bodies out of the culturing tank.

Other objects and advantages of the present invention will be apparent from the following description.

In accordance with the present invention, there is provided a culturing apparatus comprising a culturing tank for culturing cells, organs or tissue strips of a plant, internally therein, and a cutting device for cutting cultured plant bodies arranged within the culturing tank, wherein a push-out means for urging the plant bodies is further comprised against the cutting device or the cutting means is movable so as to be urged against the plant bodies.

BRIEF DESCRIPTION OF THE DRAWINGS

The present invention will be better understood from the description set forth below with reference to the accompanying drawings; in which.

DESCRIPTION OF THE PREFERRED EMBODIMENTS

As the plant to be cultured, any plant which can be cultured may be used. For example, *Lilium longiflorum Thunb.*, *Lilium speciosum Thunb.*, gladiolus, iris, chrysanthemum, and carnation, etc., can be included.

As the tissue strips of organs of plants, for example, the stalk top, stalk, leaf, flower, seed, bulbil, scale, root or other tissues cut into small strips can be used. These are generally sterilized with sodium hypochloride or ethyl alcohol, etc., before use, but the above sterilization operation is not necessary when the plants are harvested aseptically.

For cultivation, a method in which a liquid culture medium is used and a method in which a solid culture medium is used may be employed. Here the liquid culture medium may be any culture medium which can be used for the tissue culture of a plant, and examples of such a culture medium may include media prepared by adding a carbon source and plant hormones and, if necessary, vitamins and amino acids, to a Murashige-Skoog medium ('62), Rinsmeyer-Skoog medium ('65), and White medium ('63), etc.

As the solid culture medium, agar is generally used.

The culturing tank may be arranged either vertically or horizontally, and when a liquid culture medium is used, it may be either of the type which is shaken or the type in which the liquid culture medium is bubbled by aeration.

Cutting is effected, when a liquid culture medium is used, by urging the plant bodies remaining after draining the liquid culture medium from the culturing tank, after the completion of culturing, against the cutting device by a pushing means or by pushing out the culture broth together with the plant bodies by a pushing means, while discharging the culture broth. When a solid culture medium is used, the solid culture medium is generally pushed out together with the plant bodies by a pushing means, thereby urging the plant bodies against the cutting device.

Figure 1:
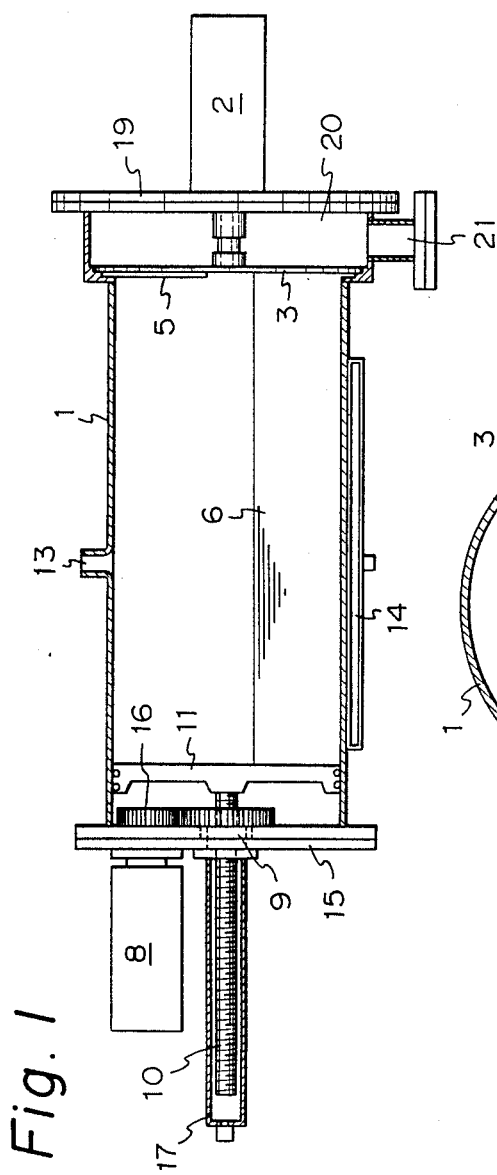
FIG. 1 is a sectional view of a culturing apparatus.
Figure 2:
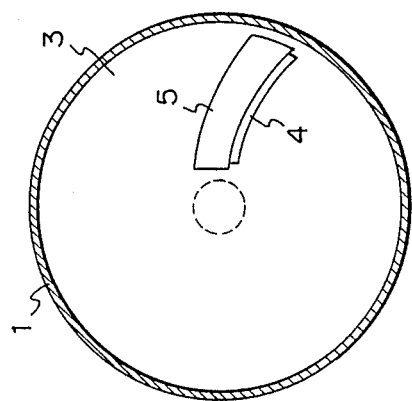
FIG. 2 is a plan view of a disc.

The cutting device differs according to whether a liquid culture medium or a solid culture medium is used. FIGS. 1 and 2 show examples of a cutting device when a liquid culture medium is used, which device comprises a disc 3 provided at one end of a cylindrical culturing tank located horizontally and driven by a motor 2 to be rotated within the vertical plane, an arc-shaped discharge groove 4 formed from the center toward the periphery of the disc 3, and a blade 5 with the edge thereof laid along the discharging groove 4. During culturing, the device is kept stationary by positioning the discharge groove 4 on the liquid culture medium 6 to prevent a leakage of the liquid through the groove 4, and during cutting, the cultured strips cut are discharged through the arc groove 4 sinking in the culture broth. As another embodiment of the cutting device, there can be included, for example, a cutting device having a fixed disc provided at one end of a horizontal culturing tank, a discharge groove formed at a portion of said disc which is dipped into the culture broth, and a blade for cutting plant bodies by rotating or reciprocating rotationally or reciprocating linearly, in which the discharge groove is blocked with the blade during culturing and the cultured strips cut during cutting allowed to pass through the discharge groove, and a cutting device having a discharge groove formed at the circumferential surface of the bottom of a cylindrical culturing tank and a blade for cutting the plant bodies by reciprocal movement in the shaft direction or in the circumferential direction along the circumferential surface, in which the discharge groove is blocked with the blade during culturing and the cultured strips cut during cutting are allowed to pass through the discharge groove.

Figure 3:
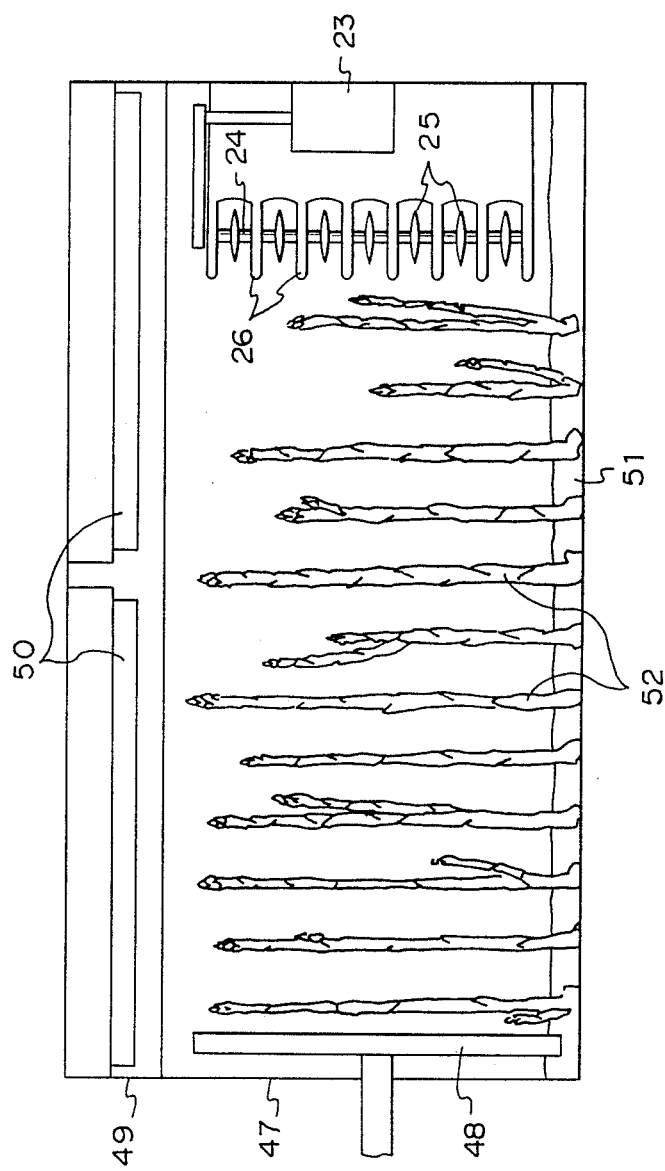
FIG. 3 is a schematic longitudinal sectional view showing another example of a culturing apparatus.
Figure 4:
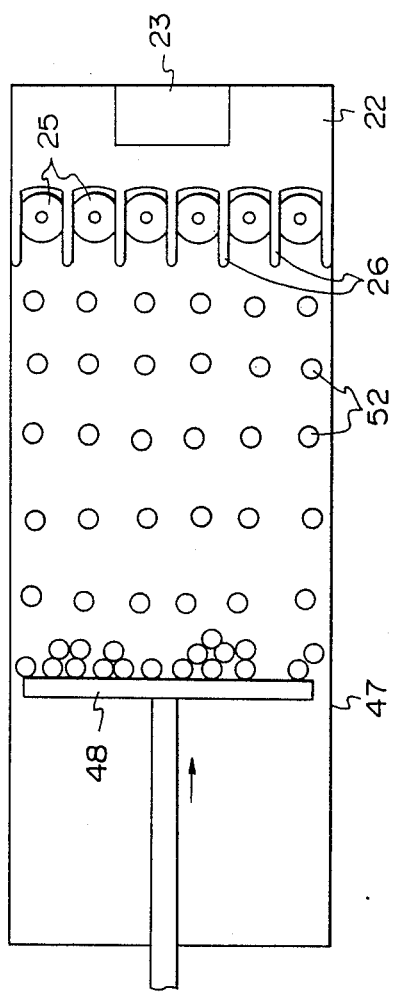
FIG. 4 is a schematic lateral sectional view of the same example.
Figure 7:
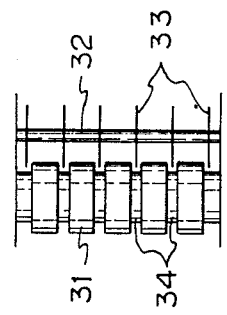
FIG. 7 is a schematic illustration showing another example.
Figure 6:
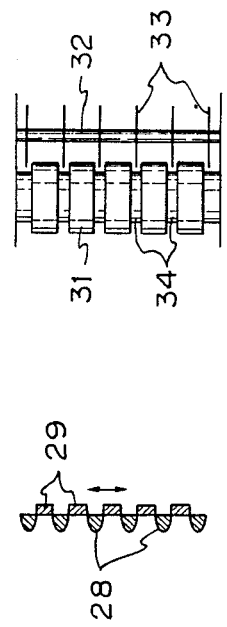
FIG. 6 is a schematic illustration showing still another example.
Figure 5:
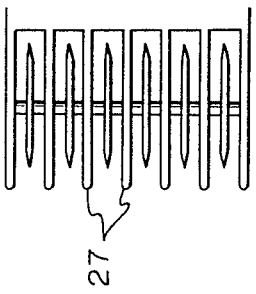
FIG. 5 is a schematic illustration showing another example of a cutting device.
Figure 8:
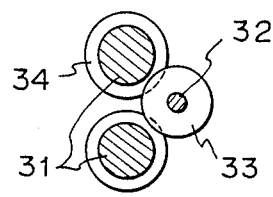
FIG. 8 is a sectional view taken along the line A—A in FIG. 7.

FIGS. 3 to 13 show cutting devices which can be used in the case of both a liquid culture medium and a solid culture medium. FIGS. 3 and 4 show an embodiment comprising rotatory blades 25, mounted at constant intervals on the respective vertical shafts 24 which are provided vertically at constant intervals, and driven rotationally and back and forth by a motor 23, and pins 26 protruded sideways from the stand 22 shaped like a comb, and through upper and lower and front and rear rotatory blades. FIG. 5 shows an embodiment wherein the pins shown in FIGS. 3 and 4 are replaced with plough plates arranged vertically in parallel at constant intervals. FIG. 6 shows an embodiment shaped like a hair clipper, comprising fixed blades 28 arranged vertically in parallel at constant intervals and movable blades 29 which move reciprocally or rockingly between the adjacent fixed blades 28 in sliding contact with the fixed blades. FIGS. 7 and 8 show an embodiment comprising rollers 31 provided at appropriate intervals and movable back and forth, and rotatory blades 33 provided on the delivery side between the rollers and mounted at constant intervals on the rotatory shaft 32 in parallel to the rollers 31, each roller 31 having a circumferential groove 34 formed thereon, and the blade tip of the rotatory blade 33 fitting freely therein. With this constitution, the rotatory blade 33 can cut plant bodies without coming into contact with the roller 31. The rotatory blade 33 in the present cutting device can be replaced with a cutting blade which moves in the right and left directions in the Figure, namely which advances and retracts with respect to the rollers 31, or alternatively a fixed blade with the blade tips mounted in parallel to the roller and a movable blade reciprocating back and forth may be provided so as to cut the plant bodies when they are delivered in a certain quantity from the roller.

Figure 9:
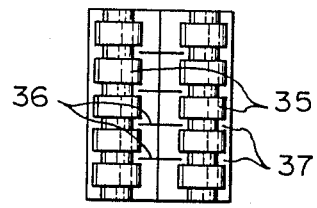
FIG. 9 is a schematic illustration viewed from the side of another cutting device.
Figure 10:
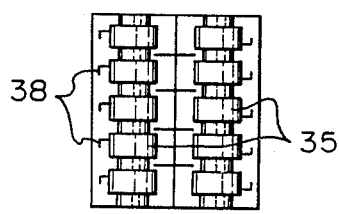
FIG. 10 is a schematic illustration of still another example.
Figure 11:
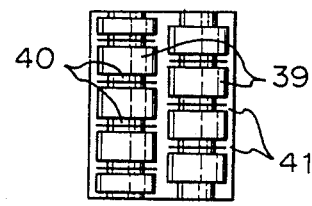
FIG. 11 is a schematic illustration of another example.

FIG. 9 shows an embodiment wherein rotatory blades 36 are arranged in a row between the rollers 35 with the blade tips of the respective rotatory blades 36 fitting freely in the circumferential grooves 37 of the rollers 35. FIG. 10 shows an embodiment wherein hooks protrude from circumferential surfaces between the grooves of the rollers 35, so as to rake in the plant bodies by hooking. FIG. 11 shows an embodiment wherein circumferential grooves 40 are formed alternately on the opposed rollers 39, and a rotatory blade 41 is protruded from the groove bottom of every circumferential groove.

Figure 12:
FIG. 12 is a schematic illustration of another cutting device.
Figure 13:
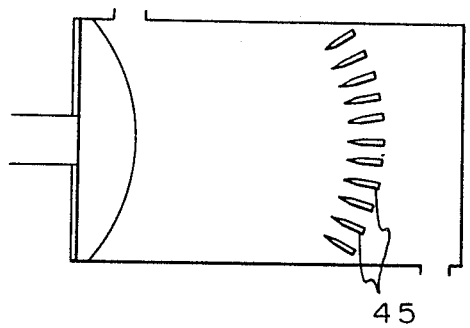
FIG. 13 is a schematic illustration of still another example.

FIG. 12 is an embodiment wherein the cutting blades 43 are provided vertically in parallel so as to push out the plant bodies. FIG. 13 is an embodiment wherein the cutting blades are arranged radially to position the blade tips on the circumferential plane. In the case of the latter cutting device, since the intervals are gradually broadened from the blade tip toward the delivery side, clogging of the plant bodies is substantially eliminated.

The cutting devices as described above are all fixed within the culturing tank, but these devices can be also made movable within the culturing tank.

When a solid culture medium is employed, the cutting device is usually provided on the solid culture medium, and only the grown plant bodies are cut.

As a pushing means for pushing out the plant bodies, compressed air also can be used, but preferably a pushing plate moving within the culturing tank is used. The pushing plate is moved in one direction by its own weight or with the addition of a weight and kept at a predetermined position by a stopper, and is allowed to move under its own weight or by the action of a spring or weight, during cutting by removing the constraint of the stopper, and further, moved by the action of an air cylinder by connecting the pushing plate to the air cylinder. Alternatively, as shown in FIGS. 1 and 2, a screw rod 10 may be protruded from the pushing plate 11 and the screw rod 10 may be advanced and retracted by rotationally driving a nut 9 screwed onto the screw rod 10, by a motor 8. When the pushing plate is moved under its own weight or by an additional weight, the movement is limited to the vertical direction, but when a spring, an air cylinder, or the mechanism shown in FIGS. 1 and 2 is used, movement is possible in either the vertical or the horizontal direction. Moreover, when an air cylinder or a screw rod is employed, the pressure on the cutting device and the size of the cut strip can be varied by changing the pushing force.

When the cutting device is constituted of cutting blades arranged radially with the blade tips arranged on the circumferential plane as shown in FIG. 13, desirably the pressing plate is formed with an arc shaped pressing surface coinciding with the above circumferential plane, whereby push cutting can be effected without leaving cutting remnants, even at the peripheral portions.

When the cutting device is movable, the pushing means can be omitted.

The cut cultured strips can be provided again for culturing after removal from the culturing tank, but preferably, are automatically transferred under an aseptic state to a subsequent culturing tank, when a plurality of culturing tanks are connected to each other, to effect culturing continuously. In this case, if the respective culturing tanks are connected under a hermetically sealed state, the culturing tanks need not be placed in an aseptic room.

When culturing has proceeded sufficiently in the culturing tank, the plant bodies are pushed out by a pushing means and urged against a cutting device, or the cutting device is moved to be urged against the plant bodies to effect cutting. The cut strips are discharged successively from the culturing tank or remain as such in the culturing tank.

According to the present invention, when the cultured plant bodies are utilized as cultured materials for further growth, compared with the prior art method in which they are once taken from the culturing tank and separated by cutting manually, it is not necessary to take them from the culturing tank, and they can be cut as is to obtain cultured cut strips. Therefore, labor saving can be effected, as this cumbersome work is eliminated, and a large amount of cultured cut strips can be easily obtained.

Also, when the culturing tank is placed horizontally, by moving a cutting device on a solid culture medium, the plant bodies can be cut without making the culturing tank larger.

Further, when the culturing tank is placed horizontally, by providing a movable blade or a fixed blade at an appropriate height, the desired site only of the grown plant bodies can be cut.

EXAMPLES

The present invention will now be further illustrated by, but is by no means limited to, the following Examples.

EXAMPLE 1

In FIGS. 1 and 2, the horizontally arranged culturing tank 1 is provided at the upper side portion with an injecting inlet 13, through which a liquid culture medium or strips of cultured materials are charged, and has a filter case 14 mounted at the lower side thereof, through which an oxygen-containing gas is fed into the liquid culture medium to effect bubbling. The nut 9 is only rotatably mounted on the tube plate 15 which closes one side of the culturing tank 1, and is driven rotatably through a gear transmission device 16 by a motor 8, and the screw rod 10 screwed into the nut 9 is covered with a pipe-shaped cover 17 having a protruding end and mounted on the tube plate 15 so that it is not contaminated by miscellaneous microorganisms.

The disc 3 driven rotatably by the motor 2 is supported axially at the other side of the culturing tank 1, and the space between the disc 3 and the tube plate 19, which closes the other side of the culturing tank 1 forms a partitioning chamber 20, and a large culturing tank not shown of another volume is connected to the discharge outlet 21 at the bottom of the partitioning plate.

The present device is constituted as described above and when the culturing has sufficiently progressed, a switch (not shown) is turned ON to drive the motors 2 and 8, thereby rotating the disc 3 and the nut 9, respectively. Accordingly, the screw rod 10 and the pushing plate 11 are moved at a constant speed toward the right in FIG. 1, to push out the cultured plant bodies and urge them toward the disc 3. The plant bodies are cut into slices by the rotating blades, and the cut strips are sent out through the arc groove 4 into the partitioning chamber 20 after cutting, and permitted to fall naturally to be passed through the discharge outlet 21 into another large culturing tank. Then culturing is repeated thereafter.

According to this Example, as described above, the cultured plants are cut as such without being taken out of the culturing tank, to obtain cultured cut strips, which strips are automatically transferred aseptically into a larger culturing tank to be further grown therein, whereby culturing can be repeated. Accordingly, after initiation of the culturing, all the culturing operations are performed automatically and aseptically, and therefore, the labor involved in the adjustment of materials and transplanting can be omitted, whereby the problems of providing labor for the bulk cultivation are solved, to allow bulk production on an industrial scale.

In the following, an experimental example of *Lilium longiflorum Thunb.*, conducted by using the present device, is shown.

EXPERIMENTAL EXAMPLE

About 300 virus-free bulbs of *Lilium longiflorum Thunb.* about 5 mm in diameter, and weighing about 900 g as the living body weight, were cut into 2 mm thick strips, and the cut strips were placed in the culturing tank 1 (volume 80 liters) shown in FIG. 1 containing 50 liters of aseptic Murashige-Skoog liquid culture medium (1962) having a pH of 5.7 and containing 4% sucrose, 0.005 mg/liter of naphthaleneacetic acid, and 0.025 g/ liter of benzyladenine.

When cultivation was carried out in a dark place at 25° C. for 3 months, while blowing 100% oxygen passed through a germ-removing filter into the medium at a rate of 5 ml/min. (oxygen movement capacity coefficient KLa: 5), about 133 small bulbs were differentiated per 1 g of the cultured cut strip. When these small bulbs were cut by the blade 5 into 2 mm thick strips, by pushing out with the pushing plate, 5400 g of aseptic cut strips were obtained. When cultivation was conducted by using the strips as seed, 130 small strips per 1 g of the cultured cut strips were obtained.

EXAMPLE 2

In FIG. 3 and FIG. 4, in the rectangular culturing tank 47 set horizontally, a cutting device was set on one side and a pushing plate 48 provided movably on the other side. A lid 49 was mounted openably on the upper side, and a fluorescent lamp 50 was located inside of the lid 49 for promoting the growth of plant bodies. Here, 51 is a liquid culture medium and 52 is the asparagus cultured in said medium.

The present device is constituted as described above, and when culturing has proceeded sufficiently, the rotatory blade 25 is rotated by driving the motor 23 and the pushing plate 48 is moved to push out the grown asparagus 52. The asparagus is pushed against the cutting device and the stalk portions are cut into pieces by the rotatory blade. The cut strips fall down and are deposited at the bottom, and the pushing plate 48 advances until coming in contact with the pins 26 and then is retracted. The lid 49 is then opened and the strips taken out. The cut strips, as in Example 1, may be also passed through the discharging outlet into another large culturing tank, where culturing is repeated.

In this Example, the cut strips are fixed and the pushing plate pushes the plant bodies against the cutting device, but in another Example, the pushing plate is omitted and the cutting device is movable. In this case, the cut strips are not deposited in one place near the cutting device but are dispersed throughout the tank. In this case, plant bodies grown in a solid culture medium can be particularly suitably cut. When only plant bodies grown from a solid culture medium are to be cut, if the cutting device is fixed, a space for pushing the solid culture medium is required on the right side of the cutting device for pushing the solid culture medium together with the plant bodies by a pushing plate, whereby a larger culturing tank must be used. In contrast, if the cutting device is moved on the solid culture medium, the culturing tank need not be made larger, and most of the culturing tank can be utilized as an effective space for culturing.

In this Example, the whole stalk portion of asparagus is cut into pieces, but in still another Example, the blade for cutting the plant bodies is provided at the bottom or at a desired height, whereby only the root portion or the portion at a desired height is cut.

We claim:

1. A culturing apparatus, comprising:
   a culturing tank for culturing in a culture medium a cellular material selected from the group consisting of cells, organs and tissue strips of a plant internally of said tank;
   a cutting means for cutting cultured plant bodies arranged within said culturing tank;
   a push-out means for urging said plant bodies against said cutting means, said push-out means being movable so as to be urged against said plant bodies; and
   feeding means for feeding an oxygen-containing gas into said culture medium.

2. A culturing apparatus as claimed in claim 1, wherein said culturing tank is horizontally arranged, a solid culture medium is used, and said cutting means moves on said solid culture medium.

3. A culturing apparatus as claimed in claim 1, wherein said culturing tank is horizontally arranged and said cutting means is a movable blade set at a desired height for cutting plant bodies grown from said culture medium at a desired site.

4. A culturing apparatus as claimed in claim 3, wherein said culture medium is a liquid culture medium.

5. A culturing apparatus as claimed in claim 3, wherein said culture medium is a solid culture medium.

6. A culturing apparatus as claimed in claim 1, wherein said culturing tank is horizontally arranged and said cutting means is a fixed blade set at a desired height for cutting plant bodies grown in said culture medium.

7. A culturing apparatus as claimed in claim 6, wherein said culture medium is a liquid culture medium.

8. A culturing apparatus as claimed in claim 6, wherein said culture medium is a solid culture medium.

9. A culturing apparatus, comprising:
   a culturing tank for culturing in a culture medium a cellular material selected from the group consisting of cells, organs and tissue strips of a plant internally of said tank, said tank consisting of a plurality of tanks connected successively from a small scale tank to a large scale tank;
   a cutting means for cutting cultured plant bodies arranged within said culturing tank; and
   a push-out means for urging said plant bodies against said cutting means, said push-out means being movable so as to be urged against said plant bodies, cultured strips cut with said cutting means being transferred aseptically to each successive culturing tank to repeatedly effect culturing.

* * * * *